United States Patent
Rasselkorde et al.

(10) Patent No.: US 8,839,673 B2
(45) Date of Patent: Sep. 23, 2014

(54) SYSTEM AND METHOD FOR INDUSTRIAL ULTRASONIC INSPECTION USING PHASED ARRAY PROBE AND DISTANCE-GAIN-SIZE FLAW SIZING

(75) Inventors: El Mahjoub Rasselkorde, Monroeville, PA (US); Waheed A. Abbasi, Murrysville, PA (US); Larry C. Himes, Greensburg, PA (US)

(73) Assignee: Siemens Energy, Inc., Orlando, FL (US)

( * ) Notice: Subject to any disclaimer, the term of this patent is extended or adjusted under 35 U.S.C. 154(b) by 360 days.

(21) Appl. No.: 13/461,854

(22) Filed: May 2, 2012

(65) Prior Publication Data

US 2013/0291640 A1    Nov. 7, 2013

(51) Int. Cl.
*G01N 29/04*    (2006.01)

(52) U.S. Cl.
USPC ............................................................ 73/625

(58) Field of Classification Search
USPC ..................... 73/625, 614, 615, 626; 702/39
See application file for complete search history.

(56) References Cited

U.S. PATENT DOCUMENTS

| | | | |
|---|---|---|---|
| 4,102,205 A * | 7/1978 | Pies et al. | 73/626 |
| 5,431,056 A * | 7/1995 | Volkmann | 73/631 |
| 5,511,425 A * | 4/1996 | Kleinert et al. | 73/627 |
| 7,017,414 B2 | 3/2006 | Falsetti et al. | |
| 7,278,289 B2 * | 10/2007 | Gessert et al. | 73/1.82 |
| 8,291,766 B2 * | 10/2012 | Engl et al. | 73/632 |
| 2008/0190205 A1 | 8/2008 | Messer et al. | |
| 2011/0016977 A1 | 1/2011 | Guracar | |
| 2011/0109627 A1 | 5/2011 | Zhang et al. | |

FOREIGN PATENT DOCUMENTS

EP    2249152 A2    11/2010

OTHER PUBLICATIONS

Certo M et al: "DGS curve evaluation applied to ultrasonic phased array testing", Insight (Non-Destructive Testing and Condition Monitoring), British Intitute of Non-DESTR Test , North Hampton, GB, vol. 52, No. 4, Apr. 1, 2010, pp. 192-194, XP008146357, ISSN 1354-2575, DOI 10 1784/ INSI.2010 52 4 192 abstract.

* cited by examiner

*Primary Examiner* — J M Saint Surin

(57) ABSTRACT

An industrial ultrasonic inspection system is capable of scanning for discontinuities in relatively thick solid objects such as solid core steel alloy turbine shafts. A phased array probe located on the turbine shaft periphery transmits ultrasonic pulses in a sector-shaped scanning field within the shaft that includes the inner 50% core volume that is of special interest in non-destructive evaluation and inspection. Staggered pulse firing alone or in combination with variable pulse repetition frequency (PRF) may be utilized in order to balance image quality with inspection speed. Discontinuities are identified by analysis of reflected echo waveform energy. Discontinuity size and position within the inspected object is correlated with an equivalent reflector size (ERS) by the Distance-Gain-Size (DGS) method.

20 Claims, 6 Drawing Sheets

PA Inspection

Conventional Inspection

SYSTEM AND METHOD FOR INDUSTRIAL ULTRASONIC INSPECTION USING PHASED ARRAY PROBE AND DISTANCE-GAIN-SIZE FLAW SIZING

BACKGROUND OF THE DISCLOSURE

1. Field of the Invention

The invention relates to non-destructive evaluation (NDE) of inanimate objects, such as solid turbine shafts and the like, by ultrasonic inspection systems and methods. More particularly the present invention relates to industrial ultrasonic inspection systems utilizing phased array inspection probes that are externally oriented about the inspected object (such as a solid turbine shaft) and that utilize Distance-Gain-Size (DGS) reflected waveform analysis techniques to correlate energy of waveforms reflected from discontinuities within the inspected object, with known energies of waveforms generated by a known size flat bottom hole (FBH) and/or side drilled hole (SDH). The discontinuity is thus correlated with pre-acquired reflected energy data (e.g., waveform amplitude) of known size holes.

2. Description of the Prior Art

NDE of an industrial object by an ultrasonic modality identifies discontinuities, such as cracks or voids, by transmission of pulsed sound waves through the object and reception of reflected "echo" waveforms. Often pulse transmission and echo reception are performed by a probe device. The reflected waveform is analyzed for acoustic patterns that are correlated with discontinuities in the inspected object. A discontinuity present in a given material will reflect a different waveform than discontinuity-free homogeneous material. Generally, relative distance between the ultrasonic probe and the discontinuity is a function of elapsed time between probe transmission of the sound wave and reception of the reflected waveform. Discontinuity physical size (i.e., its occupied volume) is indirectly correlated with the echo waveform energy (e.g., amplitude), because reflected energy is impacted by a multitude of physical factors including discontinuity physical size and dimensions, as well as attenuation of the wave energy as it travels through the inspected material.

Reflected or "echo" wave amplitude alone from a single waveform scan orientation may not provide, sufficient information to determine the estimated envelope of physical dimensions and profile of a discontinuity. Dimensional and profile information is useful for making an ultimate inspection determination whether the inspected part is acceptable to use in industrial service. In the past, analysis of a plurality reflected waveforms taken from different respective probe scan positions about the inspected object and variation of transmitted wave frequency/wavelength has enabled inspectors to construct composite spectral and/or visual images of a scanned object that correlate the approximate discontinuity size with that of a known hole size or a plurality of adjoining holes. Depending upon the physical dimensions of the scanned inanimate object and the relative dimensions of discontinuities, ultrasonic images have been constructed of sufficient resolution evaluate potential impact on the inspected part's future use in service, even though the exact physical boundaries of the discontinuity remain unknown.

A traditionally difficult to inspect service part requiring ultrasonic wave transmission over relatively, long distances is a solid steel alloy turbine shaft 10, shown in FIG. 1. Shaft 10 often has a diameter on the order of 500-1500 mm (19.7-59 inches) and often inspected with blades remaining in situ on the shaft. Relatively long sound wave transmission distances through solid steel alloy portions turbine shafts traditionally required relatively high power ultrasonic waves with a relatively high signal-to-noise ratio, all in combination leading to a lower than desired spectral or visual image resolution. It is desirable to inspect at least the inner fifty percent (50%) core internal volume 14 of the solid shaft 10 cross section. In a 500 mm diameter shaft at least a sector-shaped volume U of plus and minus 28° relative to the shaft centerline must be scanned in order to include all of the inner 50% core internal volume 14 of the shaft cross section. Required sector angle needed to scan a shaft inner core volume 14 will vary with shaft diameter.

In known conventional solid turbine shaft scanning methods, as shown in FIGS. 1 and 2, a single "straight beam" probe 20 having a 20 mm (0.79 inch) diameter capable of generating a relatively high energy sound transmission within a narrow cone beam of about 4° is positioned and scans a tangential cross-section of the turbine shaft including the inner fifty percent core volume 14. In order to complete the full tangential scan across the shaft inner volume, the probe is positioned in successive tangential scanning locations A-E. In each individual scan sequence a wedge angle block 22 is interposed between the probe 20 and the shaft surface 16 to orient the scanning beam adjacent to and slightly overlapping the prior scan beam cone. Different angle wedge blocks 22 are utilized at different respective probe scanning tangential positions A-E, necessitating a unique probe and wedge fixture setup for each position. Repetitive setup-scan-prepare the next scan setup sequences are time consuming: often requiring multiple days to complete an inspection on a single shaft. One way to reduce scanning time is to maneuver the probe 20 axially relative to the solid shaft, so that the entire axial volume of inspection interest is scanned before moving the probe to the next successive tangential position for the next set of scans. In this type of known scanning procedure a "matrix" of overlapping scans waveform data (i.e., successive tantential/axial columns of overlapping cone beam emitted by the probe) are combined to construct a single composite scanning plane inspection view of discontinuities in the region of interest. It is preferential to combine scan data from multiple scanning plane views by rotating the shaft to new circumferential positions shown by rotational angle θ and generating a new scanning plane data set for each angular rotational position. Data sets from multiple scanning plane matrices taken about the shaft circumference 16 enable construction of a three-dimensional volumetric image of the approximate correlated size of discontinuities within the shaft, especially focusing on the central 50% internal volume 14.

In industrial ultrasound modalities correlation of discontinuity size with its reflected energy traditionally has been performed by two methods: the reference block method with distance-amplitude-correction (DAC) or distance-gain-sizing (DGS). While the objective of each correlation method is to associate a flaw size echo energy reading with that of a known equivalent hole that reflects a similar energy level, each has relative benefits and disadvantages. DAC requires the use of a test block each time during the inspection. Due to the size of the rotors the DAC has to be performed using a large test block comparable to the rotor diameter. This is not practical for an in service inspection. In contrast, DGS correlation can be performed once in the laboratory and the correlation information is recorded in a spreadsheet with the correlation curves that are needed for the inspection. While the DGS method has been used in industry for a long time, determining the correlation information curves for rotors with large sound path distances (i.e., diameters) require a custom made correlation test block.

In the DGS method a calibration reference block specifically constructed with the same material matching the test object has a series of flat bottom holes (FBH) and normal to the probe scan axis (side drilled holes or SDH). The FBH are drilled at different angles in order to measure the angle amplitude correction (AAC). A 0° beam will have more beam energy than the 30° beam energy for example. All the beams need to be fired with the same amount of energy. The reference block is scanned by the probe. Reflected energy readings for each SDH individual calibration hole in the reference block are measured and converted to energy from FBHs at the same depth as the SDHs and then stored in an analyzer (often in the form of a DGS reference curve of hole size/echo amplitude for a specific distance from the probe). A discontinuity echo energy amplitude is compared manually or automatically in the analyzer with the known reference block amplitude readings for known hole sizes at the closest approximate distance. The closest size reference hole diameter is identified. Alternatively the reference information may be combined in a "pass-fail" curve establishing a maximum reference hole size at any given inspection depth within the tested object. Test objects having discontinuities below the maximum reference, hole size pass the test.

While modern automation systems greatly increase correlation of discontinuity size with a reference hole size, each DAC method inspection requires a first step of taking reference block readings at the actual inspection site before conducting a physical inspection of the test object. Field empirical testing and correlation of discontinuity and reference hole sizes by the DAC method is time consuming and subject to variances in the calibration procedure from one test site to another. An advantage of the DAC method is that all variables impacting correlation are included in the reference block calibration. In the past this advantage of all test variable inclusion has been given great importance when inspecting relatively thick test objects such as solid steel alloy turbine shafts that have required great ultrasonic pulse transmission depths.

In the DGS method, echo amplitude readings are measured for individual holes (FBH and/or SDH) that are arrayed at select distances in a calibration block and permanently stored as a set of reference curves of hole size versus distance in an analyzer. When a field inspection is performed a discontinuity's echo energy reading is compared to one or more hole size curves taken at the same distance from the probe. The discontinuity is correlated with a closest size reference hole's matching curve and/or a designated hole size pass/fail threshold may be predesignated. Discontinuities below a given threshold pass the test for future service use of the tested part. Advantages of the DGS method are elimination of field calibration of a reference block as is required by the DAC method and consistent use of the same test data curves for each inspection sequence. However, a traditional perceived disadvantage of DGS correlation methods for relatively thick test objects, such as solid steel alloy turbine shafts, was whether impact of all factors differentiating probe echo data led to sufficiently accurate correlation of the discontinuity and reference hole size. Inaccurate correlation could result in scrapping of otherwise properly serviceable parts if the test reading overstated the reference hole size or field failure of a component used in service where the correlation understated the reference hole size. Another traditional perceived disadvantage to using DGS correlation methods was the cost and effort needed to construct a large and complicated test block needed to derive the DGS calibration curve data and running the actual correlation tests.

In the past others have suggested use of phased array ultrasonic inspection probes for industrial non-destructive evaluation of components. A phased array ultrasonic probe has multiple transmitter elements that collectively sweep a series of transmitted pulses across a sector-shape swath within a test component. Thus it is suggested that a single phased array probe in a single scanning location can substitute for multiple tangential scans taken with a single element probe. One reported test procedure allegedly utilized a 32 element phased linear array ultrasonic probe and a portable phased array ultrasonic flaw detector, with DAC reference block method for correlating discontinuities and FBH reference hole size.

U.S. Pat. No. 7,017,414 states that a phased array ultrasonic probe may be placed in cavities, such as a hub bore of a turbine wheel, and the transmitted pulses selectively steered to focus on areas of interest within the wheel. The subject patent further states that a DGS technique can relate amplitude of reflected sound from the hub bore of a turbine wheel to amplitude response from known size flat bottom holes (FBH) at varying distances from the probe. It further states that DGS diagram data can be obtained through computer modeling of sound field responses or can be determined empirically using geometrically equivalent calibration blocks containing machined FBH reflectors. However, those skilled in the art know that DGS computer simulation and modeling of DGS calibration curves traditionally was done only for conventional prior art non-phased array probes. It is generally known that radial thickness dimensions from a turbine wheel central bore to its outer periphery and axial thickness are substantially less than the diameter of a solid turbine shaft, and hence generating actual calibration block DGS curves or computer modeled DGS curves for hollow, bored shafts is substantially easier than attempting to do so for large diameter turbine solid shafts.

Thus, a need exists in the art for an industrial NDE ultrasonic inspection system that facilitates quicker and simpler external scanning of interior areas of interest in solid objects without a multitude of repetitive matrix-like scanning passes tangentially across the test object.

Another need exists in the art for an industrial NDE ultrasonic inspection system that facilitates quicker and simpler external scanning of interior areas of interest in solid objects without reference block pre-calibration as is required by DAC techniques.

Yet another need exists in the art for an industrial NDE ultrasonic inspection system that facilitates quicker and simpler external scanning of interior areas of interest without either repetitive matrix-like scanning passes or reference block pre-calibration that quickly generates inspection reference information about relative location and correlated reference reflector size of discontinuities within the central core volume of a solid inspection object, such as a solid steel alloy turbine shaft, with sufficient and accurate resolution to make part serviceability inspection decisions.

SUMMARY OF THE INVENTION

Accordingly, an object of the invention is to create an industrial NDE ultrasonic inspection system that facilitates quicker and simpler external scanning of interior areas of interest in solid objects without a multitude of repetitive matrix-like scanning passes tangentially across the test object.

Another object of the present invention is to create an industrial NDE ultrasonic inspection system that facilitates quicker and simpler external scanning of interior areas of interest in solid objects without reference block pre-calibration as is required by DAC techniques.

Yet another object of the present invention is to create an industrial NDE ultrasonic inspection system that facilitates quicker and simpler external scanning of interior areas of interest without either repetitive matrix-like scanning passes or reference block pre-calibration that quickly generates inspection reference information about relative location and correlated reference reflector size of discontinuities within the central core volume of a solid inspection object, such as a solid steel alloy turbine shaft, with sufficient and accurate resolution to make part serviceability inspection decisions.

These and other objects are achieved in accordance with the present invention by an industrial ultrasonic inspection system that identifies discontinuities in relatively thick solid objects such as solid core steel alloy turbine shafts. A phased array probe located on the turbine shaft periphery transmits ultrasonic pulses in a sector-shaped scanning field within the shaft that includes the inner 50% core volume that is of special interest in non-destructive evaluation and inspection. Discontinuities are identified by analysis of reflected echo waveform energy. Staggered pulse firing of the phased array probe, or variable pulse repetition frequency (PRF) may be utilized jointly or severally, in order to minimize so-called "ghost" echo distortion of scan collection data. Either staggered pulse firing or variable PRF, alone or in combination, balance image quality with inspection speed by increasing sectoral angle between sequential firing pulses and/or adjusting the PRF as is needed during the scan cycle. Abnormality size and position within the inspected object are correlated with an equivalent reflector size by the Distance-Gain-Size (DGS) method.

In some embodiments, the present invention features an ultrasonic inspection system for the non-destructive evaluation of an inanimate object including a phased-array ultrasonic inspection probe for scanning an internal volume of an inanimate scanned object, the scanning penetrating at least fifty percent (50%) of central internal volume when oriented in a first stationary probe position external to an exterior periphery of the inanimate object. The probe has a plurality of transmitters for transmitting a series of ultrasonic waves through the internal volume at varying sectorial angles, and a plurality of receivers for receiving reflected waveforms. The system includes an inspection fixture for moving and selectively orienting the probe at a plurality of scanning positions about the exterior periphery. A data acquisition system is coupled to the probe receiver, for acquiring reflected waveform receipt time and amplitude data collected at the plurality of probe scanning positions about the exterior periphery and creating waveform data sets correlated with the scanning positions. A data analysis system is coupled to the data acquisition system for identifying a discontinuity in the internal volume and for correlating reflected waveform data sets with a size and a position of the identified discontinuity using a Distance-Gain-Size analysis technique. Energy data within the reflected waveform data sets are compared to pre-stored energy response data from a known equivalent reflector size (ERS) at varying distances from the probe receivers, that are flat bottom holes (FBH) and side drilled holes (SDH).

In other embodiments, the present invention features an ultrasonic inspection system for the non-destructive evaluation of an inanimate object, including a phased-array ultrasonic inspection probe for scanning an internal volume of the inanimate scanned object. In this embodiment the probe has a plurality of transmitters for transmitting a series of ultrasonic waves in a staggered sequential pattern through the internal volume at varying sectorial angles into non-adjoining portions of the internal volume, and a plurality of receivers for receiving reflected waveforms. This embodiment of the present invention includes an inspection fixture for moving and selectively orienting the probe at a plurality of scanning positions about the exterior periphery. A data acquisition system is coupled to the probe receiver, for acquiring reflected waveform receipt time and amplitude data collected at the plurality of probe scanning positions about the exterior periphery and creating waveform data sets correlated with the scanning positions. A data analysis system is coupled to the data acquisition system for identifying a discontinuity in the internal volume and for correlating reflected waveform data sets with a size and a position of the identified discontinuity using a Distance-Gain-Size analysis technique. Energy data within the reflected waveform data sets are compared to pre-stored energy response data from a known equivalent reflector size (ERS) at varying distances from the probe receivers, the ERS selected from the group consisting of flat bottom holes (FEE) and side drilled holes (SDH).

The present invention also is directed to a method for performing an ultrasonic inspection for non-destructive evaluation of an inanimate object. The method comprises scanning an internal volume of an inanimate scanned object with a phased-array ultrasonic oriented at a first stationary probe position external to an external periphery of the inanimate object. The probe has a plurality of transmitters for transmitting a series of ultrasonic waves through the internal volume at varying sectorial angles, and a plurality of receivers for receiving reflected waveforms therefrom. The probe is selectively moved and oriented at a plurality of scanning positions about the exterior periphery. Reflected waveform receipt time and amplitude data are acquired and collected at the plurality of probe scanning positions about the exterior periphery. Waveform data sets are created and correlated with the scanning positions with a data acquisition system. A data analysis system is used for identifying a discontinuity in the internal volume and correlating reflected waveform data sets with a size and a position of the identified discontinuity using a Distance-Gain-Size (DGS) analysis technique. Using the DGS technique, energy data within the reflected waveform data sets are compared to pre-stored energy response data from a known equivalent reflector size (ERS) at varying distances from the probe receivers, the ERS selected from the group consisting of flat bottom holes (FBH) and side drilled holes (SDH).

The objects and features of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of the present invention can be readily utilized in industrial ultrasonic inspection systems and methods that identify discontinuities in relatively thick solid objects such as solid core steel alloy turbine shafts, with relatively fast inspection speeds. A phased array probe facilitates a large scan volume that incorporates the central core volume of the inspected object in a single scan pass. Utilization of Distance-Gain-Size discontinuity evaluation methods correlates discontinuity with equivalent reflector size holes without the need to perform pre-scan reference block calibration.

Figure 3:
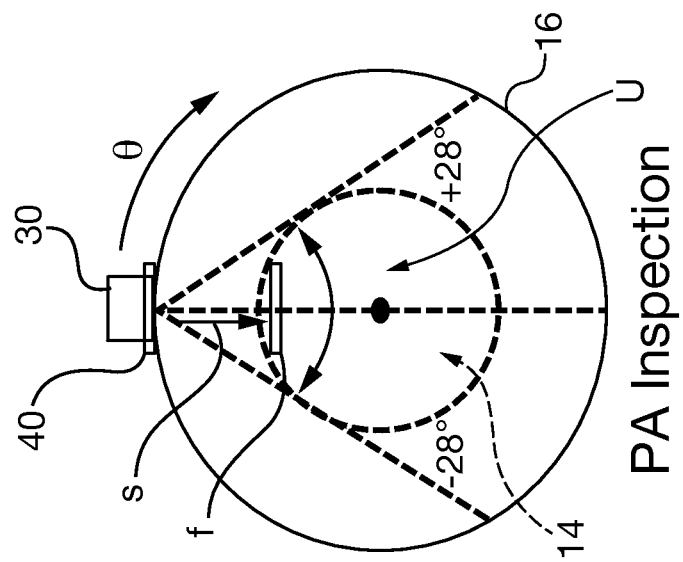
FIG. 3 shows a scanning pattern of the present invention being performed with a multiple detector phased array ultrasonic probe on a solid shaft of the general type of FIG. 1.
Figure 2:
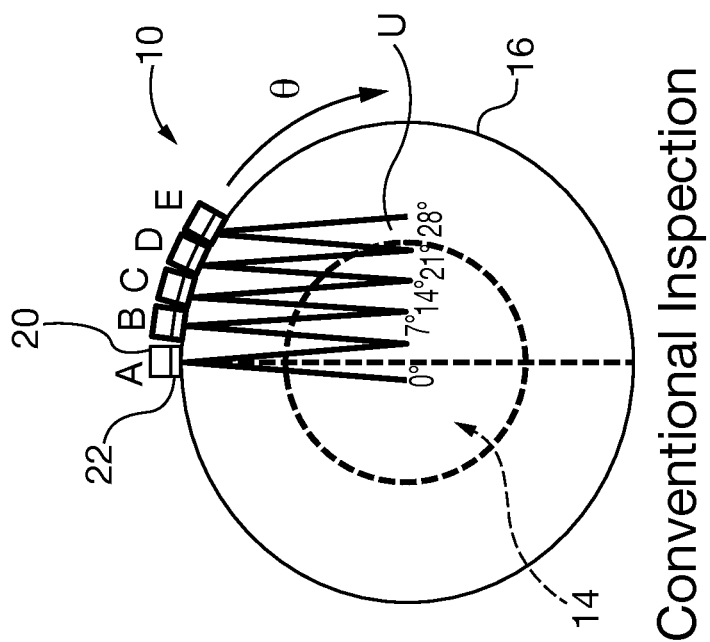
FIG. 2 shows a known scanning pattern being performed with a single detector ultrasonic probe on a solid shaft of the general type of FIG. 1.
Figure 4:
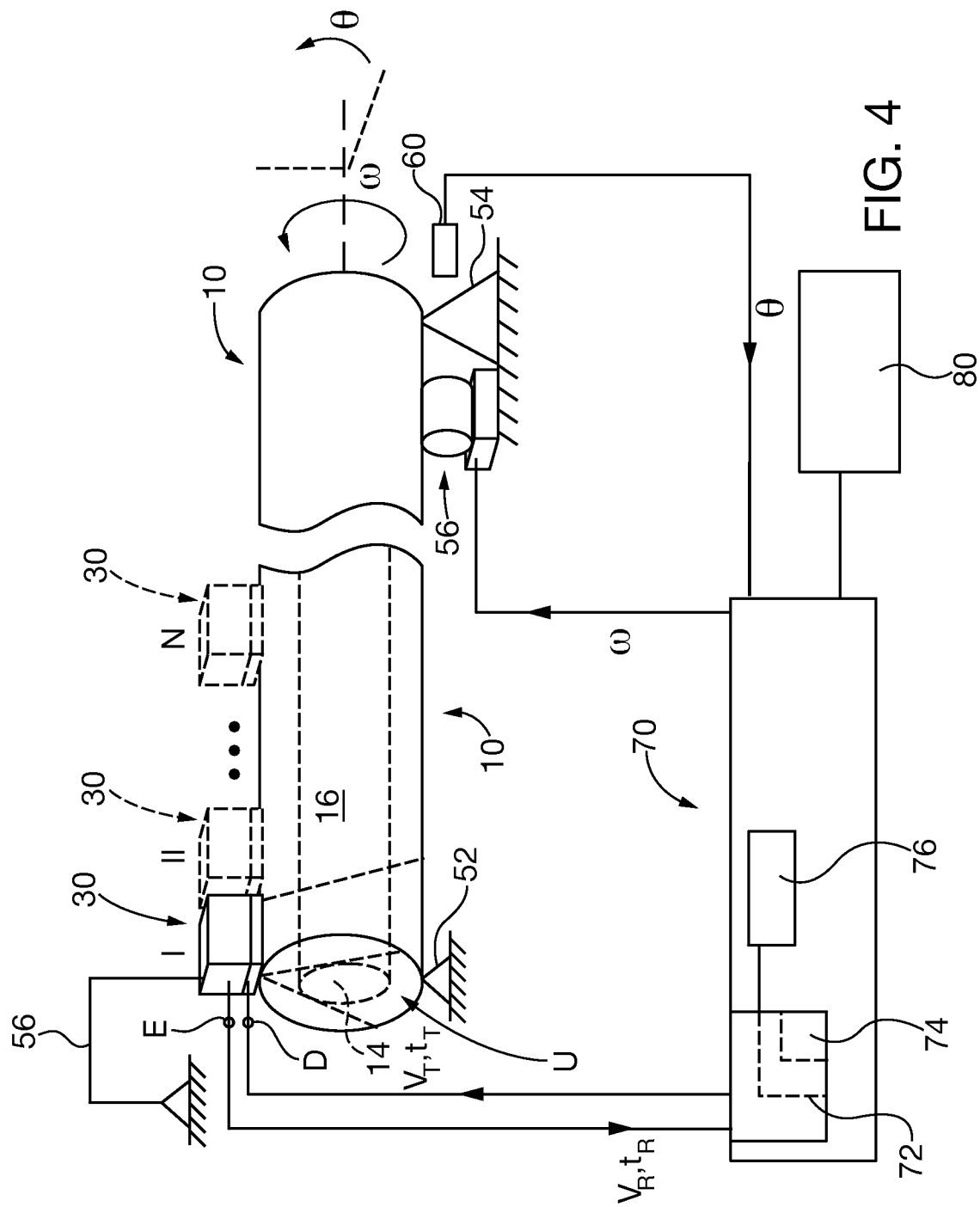
FIG. 4 shows a schematic block diagram of a solid turbine shaft inspection system of the present invention.

Referring to FIGS. 3 and 4, an exemplary solid core steel alloy shaft 10 is ultrasonically inspected with phased array probe 30. In the case of an approximately 500 mm diameter shaft, the probe 30 sweeps a −28° to +28° sector shaped scan volume U relative to the shaft 10 axial centerline, encompassing the central core volume 14. A wedge block 40 optionally is interposed between the probe 30 and the shaft circumferential surface in order to protect the probe from damage. A discontinuity f in the shaft is located a radial distance s from the probe 30.

The phased array probe 30 includes a linear array of functional transmitters and receivers 32/34 (shown functionally and schematically as separate components, but in reality often the same component is periodically switched between transmit and receive modes), each having a plurality of channels, with 4, 8, 16 and 32 channels being commonly commercially available. A suitable phased array probe is a 16 channel DGS probe sold by Imasonic SA of Voray sur l'Ognon, France, with a 2 MHz central frequency, bandwidth greater than 40% and a pulse width of less than 2 μs. The transmitters 32 sequentially transmit sound wave pulses having an energy $V_T$ (dB) at a pulse rate $t_T$ that propagate through the shaft 10 and reflect back to the receivers 34 as a reflected waveform with energy $V_R$ and time delay $t_R$. The receivers capture the reflected waveform data set for further processing by the inspection system. The relatively high bandwidth of the phased array probe 30 enables focusing of the ultrasonic beam so that there is ultimately better resolution of detected flaws.

Figure 1:
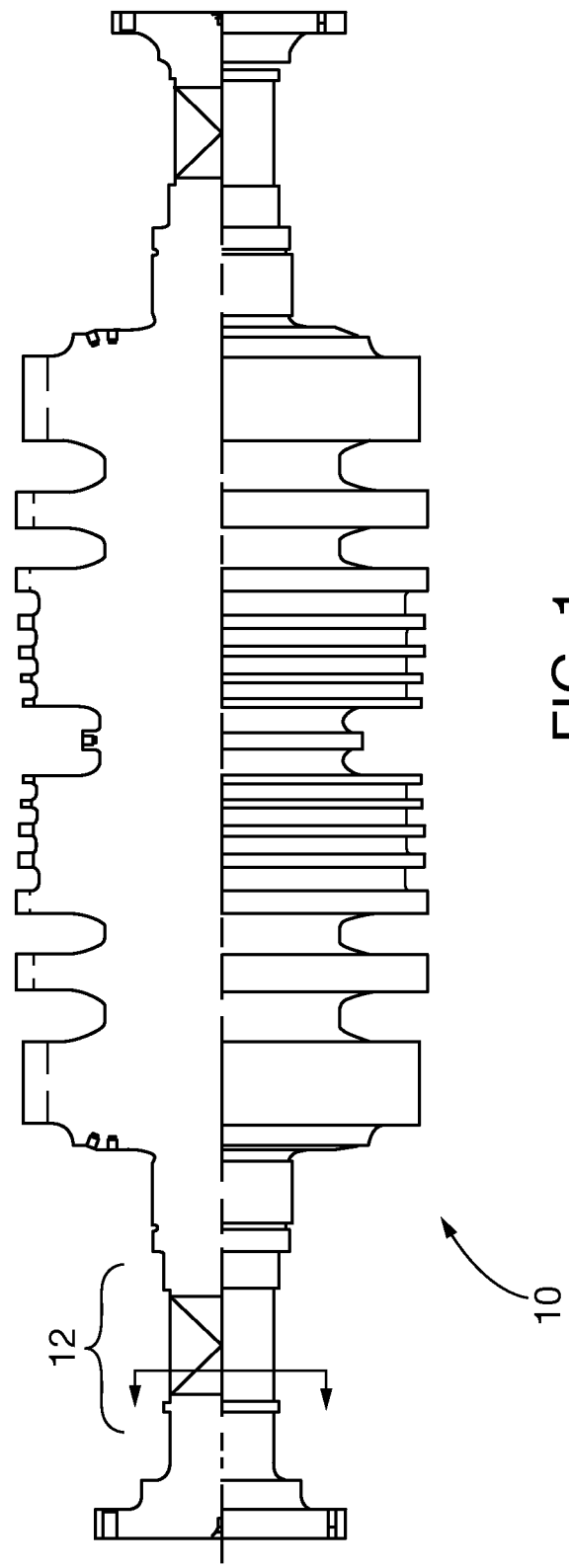
FIG. 1 shows an exemplary known solid steel alloy turbine shaft.
Figure 5:
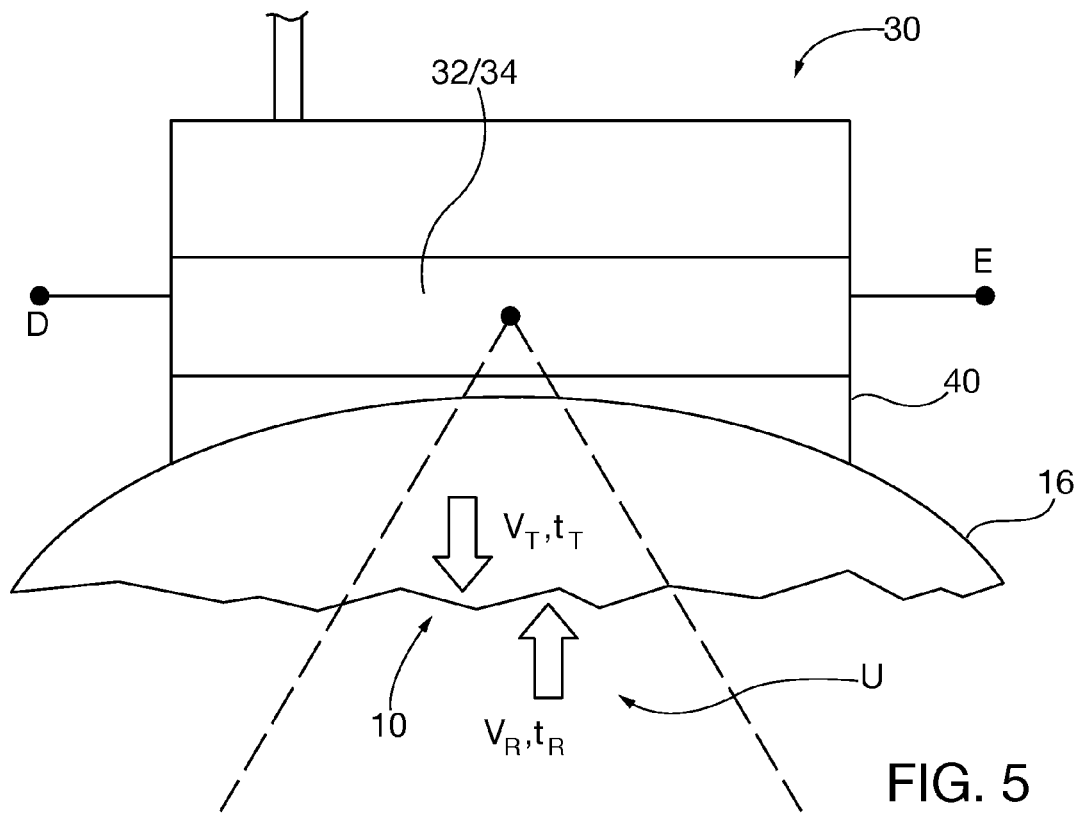
FIG. 5 shows a schematic block diagram of a phased array probe used in the system of FIG. 4.
Figure 5A:
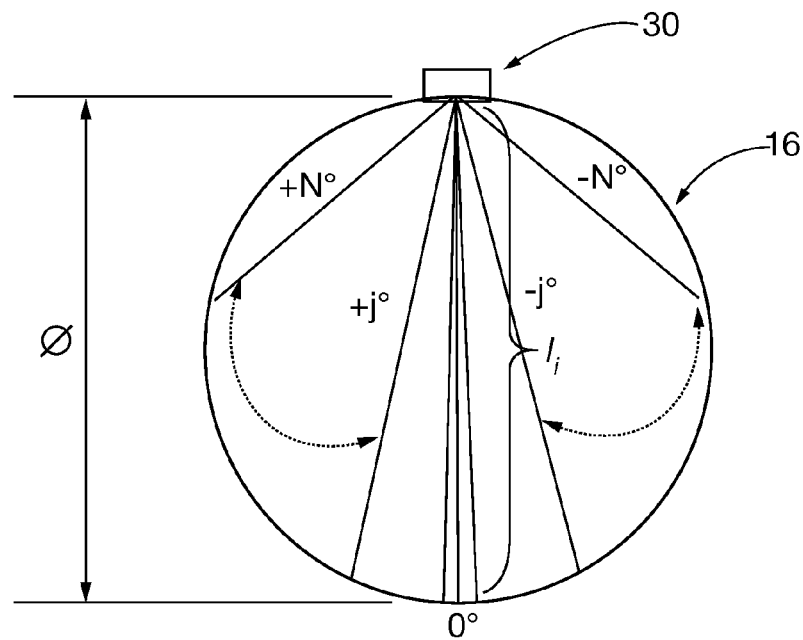
FIG. 5A shows the relationship between scanning pattern angular position and variable pulse repetition frequency (PRF) pulsing mode used by the phased array probe of FIG. 5.

When performing an ultrasonic scan on a relatively large diameter object, such as the exemplary solid turbine shaft 10, so-called "ghost" or phantom echoes can cause a misinterpretation of the reflected waveform data received by the receivers 34. Referring to FIG. 5A, one commonly known scanning method to reduce likelihood of ghost echo data misinterpretation is by using a low scanning pulse repetition frequency (PRF), so that the ghost echo propagation attenuates or ceases prior to the next pulse transmission and receipt sequence. The ultrasonic probe 30-transmitter longitudinal wave is usually used for the ultrasonic inspection of large forging turbine shaft 10. For each sound beam the system has to adjust the time interval $t_i$ for the pulse transmission in a way to avoid ghost echoes (see FIG. 1 for more details). Usually the time interval is set up to $60 \times t_i$ in order to avoid the ghost echoes. The time interval $t_i$ is directly related to v=5920 m/s the longitudinal sound of steel, and the sound path length ø (diameter in millimeters of the rotor shaft 10), in accordance with the following equation (1):

$$PRF(\text{Hz}) = 8.3 \times \frac{v}{\phi} \qquad (1)$$

Thus, in a 2000 mm diameter shaft the PRF is maintained below 24 Hz. For a phased array sectoral scan with 2×N+1 beams, the system has to keep a PRF of 24 Hz from each pulse firing shot to the next one, and also needs to perform each of the 2×N+1 beam orientation firing shots before moving to next angular scanning position e in the circumferential direction. This makes the acquisition of the data very slow. The present invention greatly increases data acquisition scanning speed through use of either staggered pulse firing of the phased array probe or with variable pulse repetition frequency (PRF), jointly or severally, as described below.

Staggered probe 30 pulse firing is accomplished by staggering the firing of the individual transmitters in the transmitter array 32 so that there is a greater sectoral angular divergence between firing pulses than compared to sequentially firing adjacent individual transmitters, as is traditionally done in phased array probes 30. For example, in a traditional scan sequence of the shaft 10 in FIG. 5, the probe 30 fires individual transmitters sequentially from −28° to +28°. In contrast, an exemplary staggered firing pulse option for probe 30 when practicing the present invention is to fire a first pulse at −28°, the next pulse at +1°, the next at −27°, the next at +2°, etc. Thus when performing staggered pulse firing, there is less likelihood that a ghost echo generated in one firing pulse will impact the next firing pulse's data acquisition.

The other optional data scanning procedure practiced in the present invention is variable PRF. Referring back to FIG. 5A, scanning beams that are near the 0° sectoral scanning direction are very sensitive to each other since the sound path is very close. Therefore most of the ghost echoes are presented around the 0° direction. By varying the PRF by discrete values during the sectoral scan, for example using a small value for the ultrasonic beams around 0° direction and increasing the PRF for the rest of ultrasonic beams firing sectorial orientations, the overall scanning time per aggregate sectoral scan can be reduced, as is demonstrated by the following equation (2):

$$\begin{cases} PRF = \text{Min}\{PRF\} & -j < i < +j \\ PRF = m \times \text{Min}\{PRF\} & -(j+1) < i < -N \ \& \ j+1 < l < +N \end{cases} \qquad (2)$$
$$m = \{10 \ldots 100\}$$

Another variable PRF method is to use a linear relationship on the PRF value for the ghost echoes area instead of fixed small value of the PRF, as is demonstrated by the following equation (3):

$$\begin{cases} PRF(i) = i \times \text{Min}\{PRF\} & -j < i < +j \\ PRF = m \times \text{Min}\{PRF\} & -(j+1) < i < -N \ \& \ j+1 < l < +N \end{cases} \quad (3)$$

$$m = \{10 \ldots 100\}$$

Once a sectoral scan is completed the shaft 10 is rotated to a new angular position θ in order to acquire the next data set. To acquire the new angular position θ, shaft 10 is rotatively supported on a fixture that includes stands 52, 54, and selectively rotated by driven roller 56 as depicted by ω to selected angular positions θ. Probe fixture 58 orients the phased array probe 30 at a desired position along the shaft 10 circumference 16. The shaft 10 rotated, with angular position encoder 60 identifying shaft angular position θ. Upon completion of a full 360° rotation of shaft 10 the probe 30 has generated a pulsed transmitted waveform data set (actually recorded or derived from previously known probe pulsing rate and output energy levels) and a reflected echo waveform energy data set corresponding to each scanned angular position θ. The waveform data sets include energy (V), time (t) and angular position (θ) information. Upon completion of a full 360° scan, depicted as I in FIG. 4, the phased array probe 30 is positioned in a second axial position II so that its scanned volume U overlaps that of the scanned volume of position I. Thereafter a 360° scan and data set collection is performed at position II and the sequence repeated until full inspection of the designated inspection volume is completed at position N. Acquired scanned data sets are analyzed to identify potential flaws within the scanned shaft 10.

Ultrasonic inspection analyzer 70 is communicatively coupled to the phased array probe 30, the shaft drive 56 and the position encoder 60 by known means, such as cables. The phased array probe 30 routes acquired scan waveform data sets to the analyzer 70. A suitable analyzer 70 is a dedicated electronic device, such as a DYNARAY® Phased Array instrument from Zetec, Inc. of Snoqualmie, Wash., USA, or a general purpose computer. Either type device preferably has a processor 72 including known software instruction modules 74 stored in memory 76 that when executed by the processor correlate scanned waveform data sets with position and size of discontinuities within the inspected shaft 10 by means of Distance-Gain-Size (DGS) correlation methods. The analyzer 70 may utilize Zetec, Inc. UltraVision® 3 data acquisition and visualization software module and/or the AutoNDE SR™ three-dimensional visualization and data analysis software module available from Siemens Energy, Inc. of Orlando, Fla. A description of some functional features of the Siemens AutoNDE SR™ software package appear in United States Patent Application Publication No. US2011/0109627, published May 12, 2011, the entire contents of which are incorporated herein by reference as if fully set forth herein. published description Discontinuity information is available for operator inspection at human machine interface 80, that may include any combination of visual display, touch screen, smart tablet, smart phone, keypad or keyboard, mouse or other known pointing device.

It is also to be understood that the present invention analyzer 70 may be implemented in various forms of hardware, software, firmware, special purpose processors, or a combination thereof. Preferably, as noted above, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device, or as also noted above a human machine interface.

Figure 6:
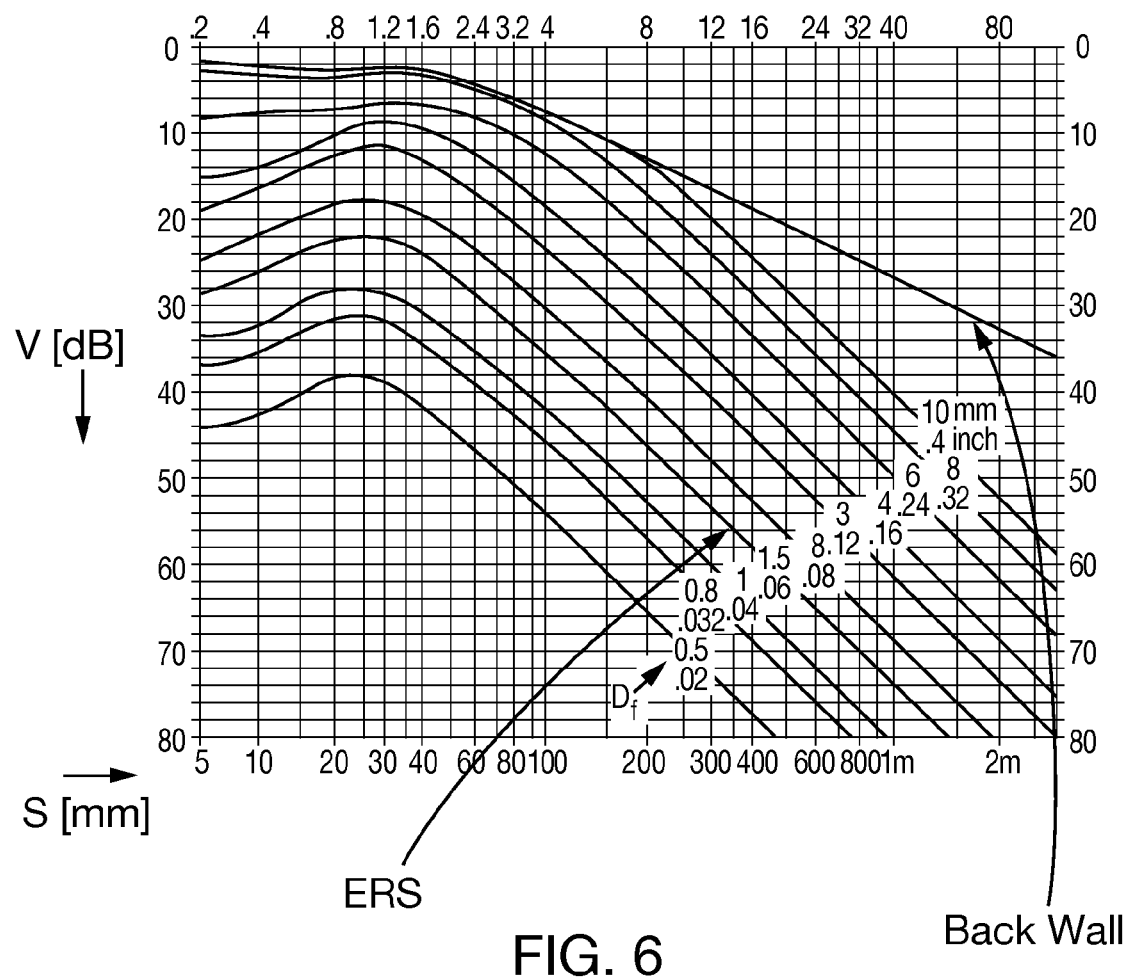
FIG. 6 shows an exemplary-Distance-Gain-Size (DGS) for illustrating correlation of a discontinuity with an equivalent reference size (ERS) reflector circular disc or hole)

FIG. 6 shows conceptually a set of DGS curves that graphically depict reflected waveform energy intensity V (in dB) and distance s from the phased array probe 30. Each of the successive series of curves is generated for different respective diameters of equivalent reflector size (ERS) circular discs that have been correlated for different diameter flat bottom holes (FBH) or side drilled holes (SDH). The back wall denotes the reflection curve for the opposite circumferential surface of the shaft 10. A shaft 10 that is devoid of discontinuities will propagate a sound pulse of intensity and duration depicted by the back wall curve. Discontinuities will reflect a waveform with energy differing from the backwall curve. Those waveforms are analyzed using the DGS method and the discontinuity or aberration energy wave form correlated with a corresponding ERS energy level. The ERS energy levels are in turn correlated with the energy waveform of a FBH or SDH so that an inspector can roughly determine the discontinuity equivalent physical size.

Figure 7:
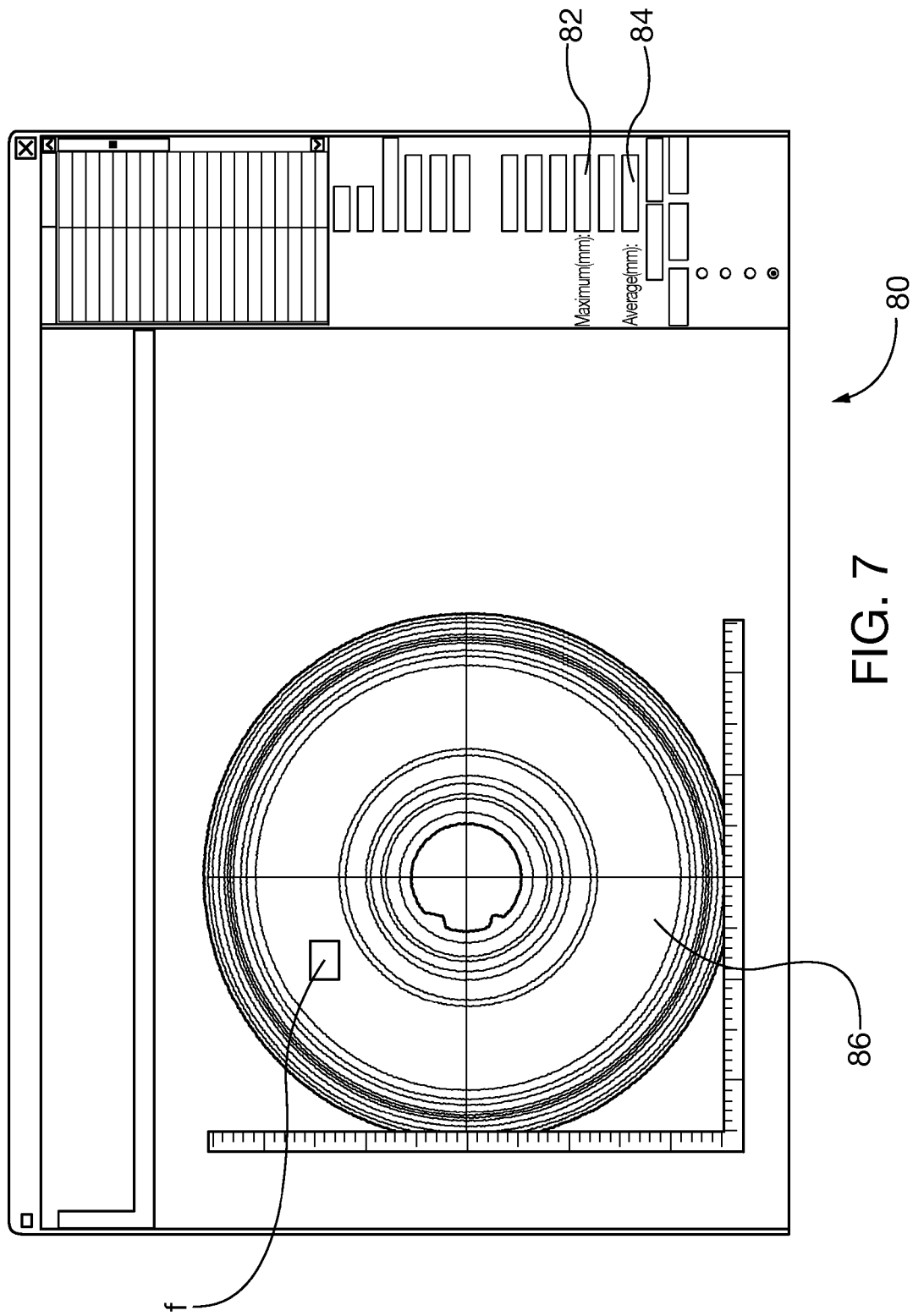
FIG. 7 is an exemplary visual display image of ultrasonic inspection results on a turbine shaft, showing tabular estimation of maximum ERS for any discontinuity and a constructed image thereof showing correlated size and location of discontinuities.

As shown in FIG. 7, discontinuity data from collective scan data sets can be analyzed for useful inspection information. Exemplary inspection information tools for shaft 10 or other inanimate object inspection include maximum identified flaw size 82, average flaw size 84 or a virtual image 86 that displays the discontinuity f.

Discontinuity data from the collective scan data sets are analyzed for useful inspection information by one or more software module instruction sets 74 that are executed within the analyzer 70 processor. Previously described exemplary software modules for NDE analysis include the Zetec, Inc. UltraVision® 3 data acquisition and visualization software module and/or the AutoNDE SR™ three-dimensional visualization and data analysis software module available from Siemens Energy, Inc. of Orlando, Fla.

Although various embodiments which incorporate the teachings of the present invention have been shown and described in detail herein, those skilled in the art can readily devise many other varied embodiments that still incorporate these teachings. It is to be understood that, because some of the constituent system components and method steps depicted in the accompanying figures are preferably implemented in software, the actual connections between the system components (or the process steps) may differ depending upon the manner in which the present invention is programmed. Specifically, any of the computers or devices may be interconnected using any existing or later-discovered networking technology and may also all be connected through a lager network system, such as a corporate network, metropolitan network or a global network, such as the Internet.

What is claimed is:

1. An ultrasonic inspection system for the non-destructive evaluation of an inanimate object comprising:
   a phased-array ultrasonic inspection probe for scanning an internal volume of an inanimate scanned object, the scanning penetrating at least fifty percent (50%) of central internal volume when oriented in a first stationary probe position external to an exterior periphery of the inanimate object, the probe having a plurality of transmitters for transmitting a series of ultrasonic waves through the internal volume at varying sectorial angles, and a plurality of receivers for receiving reflected waveforms therefrom;

an inspection fixture for moving and selectively orienting the probe at a plurality of scanning positions about the exterior periphery;

a data acquisition system coupled to the probe receiver, for acquiring reflected waveform receipt time and amplitude data collected at the plurality of probe scanning positions about the exterior periphery and creating waveform data sets correlated with the scanning positions;

a data analysis system coupled to the data acquisition system for identifying a discontinuity in the internal volume and for correlating reflected waveform data sets with a size and a position of the identified discontinuity using a Distance-Gain-Size analysis technique, wherein energy data within the reflected waveform data sets are compared to pre-stored energy response data from a known equivalent reflector size (ERS) at varying distances from the probe receivers, the ERS selected from the group consisting of flat bottom holes (FBH) and side drilled holes (SDH).

2. The system of claim 1, wherein the inspection probe transmitters stagger ultrasonic wave transmission sectorial angles into non-adjoining portions of the internal volume of the scanned object.

3. The system of claim 2, wherein the inspection probe comprises a linear array of transmitters that do not transmit sequentially in adjoining order.

4. The system of claim 3, wherein the linear array of transmitters is divided on opposite sides into first and second zones, and the respective zones transmit sequentially.

5. The system of claim 2, wherein the staggered sectorial angles sequentially shift back and forth between opposite zones of the central internal volume.

6. The system of claim 5, wherein the staggered sectorial angles shift back and forth symmetrically between zones.

7. The system of claim 2, wherein at least one respective inspection probe transmitter is pulsed at different pulse repetition frequencies (PRFs) than at least one other transmitter.

8. The system of claim 7, wherein the PRF for each transmitter is chosen as a function of sectorial angle and scanned object penetration depth.

9. The system of claim 1, wherein at least one respective inspection probe transmitter is pulsed at different pulse repetition frequencies (PRFs) than at least one other transmitter.

10. The system of claim 9, wherein the PRF for each transmitter is chosen as a function of sectorial angle and scanned object penetration depth.

11. An ultrasonic inspection system for the non-destructive evaluation of an inanimate object comprising:

a phased-array ultrasonic inspection probe for scanning an internal volume of an inanimate scanned object, the probe having a plurality of transmitters for transmitting a series of ultrasonic waves in a staggered sequential pattern through the internal volume at varying sectorial angles into non-adjoining portions of the internal volume, and a plurality of receivers for receiving reflected waveforms therefrom;

an inspection fixture for moving and selectively orienting the probe at a plurality of scanning positions about the exterior periphery;

a data acquisition system coupled to the probe receiver, for acquiring reflected waveform receipt time and amplitude data collected at the plurality of probe scanning positions about the exterior periphery and creating waveform data sets correlated with the scanning positions;

a data analysis system coupled to the data acquisition system for identifying a discontinuity in the internal volume and for correlating reflected waveform data sets with a size and a position of the identified discontinuity using a Distance-Gain-Size analysis technique, wherein energy data within the reflected waveform data sets are compared to pre-stored energy response data from a known equivalent reflector size (ERS) at varying distances from the probe receivers, the ERS selected from the group consisting of flat bottom holes (FBH) and side drilled holes (SDH).

12. The system of claim 11, wherein at least one respective inspection probe transmitter is pulsed at different pulse repetition frequencies (PRFs) than at least one other transmitter.

13. The system of claim 12, wherein the PRF for each transmitter is chosen as a function of sectorial angle and scanned object penetration depth.

14. A method for performing an ultrasonic inspection for non-destructive evaluation of an inanimate object comprising:

scanning an internal volume of an inanimate scanned object with a phased-array ultrasonic oriented at a first stationary probe position external to an external periphery of the inanimate object, the probe having a plurality of transmitters for transmitting a series of ultrasonic waves through the internal volume at varying sectorial angles, and a plurality of receivers for receiving reflected waveforms therefrom;

moving and selectively orienting the probe at a plurality of scanning positions about the exterior periphery;

acquiring reflected waveform receipt time and amplitude data collected at the plurality of probe scanning positions about the exterior periphery and creating waveform data sets correlated with the scanning positions with a data acquisition system; and identifying with a data analysis system a discontinuity in the internal volume and correlating reflected waveform data sets with a size and a position of the identified discontinuity using a Distance-Gain-Size analysis technique, wherein energy data within the reflected waveform data sets are compared to pre-stored energy response data from a known equivalent reflector size (ERS) at varying distances from the probe receivers, the ERS selected from the group consisting of flat bottom holes (FBH) and side drilled holes (SDH).

15. The method of claim 14, wherein the transmitting step is performed by staggering ultrasonic wave transmissions at separated sectorial angles into non-adjoining portions of the internal volume of the scanned object.

16. The method of claim 15, wherein the staggered sectorial angles sequentially shift back and forth between opposite zones of the central internal volume.

17. The method of claim 15, wherein at least one respective inspection probe transmitter is pulsed at different pulse repetition frequencies (PRFs) than at least one other transmitter.

18. The method of The system of claim 17, wherein the PRF for each transmitter is chosen as a function of sectorial angle and scanned object penetration depth.

19. The method of claim 14, wherein at least one respective inspection probe transmitter is pulsed at different pulse repetition frequencies (PRFs) than at least one other transmitter.

20. The method of The system of claim 18, wherein the PRF for each transmitter is chosen as a function of sectorial angle and scanned object penetration depth.

\* \* \* \* \*